United States Patent [19]

Demain et al.

[11] 4,245,046

[45] Jan. 13, 1981

[54] PROCESS FOR THE FERMENTATIVE PRODUCTION OF XANTHAN GUM WITH ORGANIC ACIDS

[75] Inventors: Arnold L. Demain, Wellesley, Mass.; Peter Souw, Muenster, Fed. Rep. of Germany

[73] Assignee: Massachusetts Institute of Technology, Cambridge, Mass.

[21] Appl. No.: 23,213

[22] Filed: Mar. 23, 1979

[51] Int. Cl.$^3$ ................................................ C09J 3/02
[52] U.S. Cl. ..................................... 435/104; 435/910
[58] Field of Search .............................. 435/104, 910

[56] References Cited

U.S. PATENT DOCUMENTS 4,119,546  10/1978  Wernau .............................. 435/104 X

*Primary Examiner*—Thomas G. Wyse
*Attorney, Agent, or Firm*—Arthur A. Smith, Jr.; Paul J. Cook

[57] ABSTRACT

Xanthan gum is produced by fermentation with the bacterium, *Xanthomonas campestris* NRRL B-1459, of a nutrient medium containing a sugar and a stimulatory organic acid which stimulates the production of xanthan gum. The stimulatory organic acid can be a source of pyruvic acid, alpha-keto-glutaric acid, succinic acid or mixtures thereof.

6 Claims, No Drawings

PROCESS FOR THE FERMENTATIVE PRODUCTION OF XANTHAN GUM WITH ORGANIC ACIDS

BACKGROUND OF THE INVENTION

This invention relates to a process for producing xanthan gum from *Xanthomonas campestris* NRRL B-1459.

Polysaccharides or gums that function to control the flow properties of aqueous systems have a wide variety of uses including oil well drilling and fracturing, food additives, textile printing, paint additives and the like. Of the presently employed polysaccharides or gums, the most widely used is xanthan gum which is derived from a sugar or starch by fermentation with *Xanthomonas campestris*. Xanthan gum dissolves in water to produce a high viscosity solution at very low concentrations and has the property of controlling rheological properties of fluids. Xanthan gum solutions are highly pseudoplastic in that the viscosity decreases rapidly as the rate of shear on the solution is increased. This relationship is instantaneous and reversible. In contrast to most polysaccharides, the viscosity of xanthan gum solutions is essentially constant over the range of about 25° F. to about 200° F. In addition, xanthan gum has excellent thermal stability and maintains its viscosity even when salts such as sodium chloride are added thereto. Because of these properties, xanthan gum has been the thickener of choice particularly in oil well drilling fluids and in oil recovery processes as well as in a wide variety of other industrial applications.

Xanthan gum presently is produced by an aerobic submerged fermentation in a medium containing a carbon source such as 1–5% glucose. Upon completion of the fermentation, the fermentation liquor is pasteurized and the polysaccharide is recovered by precipitation such as with an alcohol, e.g. methanol, ethanol, isopropyl alcohol. The resultant gum product then is dried and milled and is useful for forming high viscosity solutions.

It would be highly desirable to provide a means for stimulating the production of xanthan by the fermentation of *Xanthomonas campestris*. Such a process would provide higher yields of the gum thereby obtaining substantial economic benefit and improved efficiencies in the production of xanthan gum.

SUMMARY OF THE INVENTION

This invention provides a process for the production of xanthan gum by the fermentation of *Xanthomonas campestris* NRRL B-1459 wherein conversion of the carbon source or carbon sources to xanthan gum is stimulated by one or a mixture of certain organic acids. The organic acids have been found to stimulate the conversion of the carbon source in the fermentation liquor to xanthan gum rather than comprising a substitute for the conventional carbon sources in the fermentation liquor. It has been found that the inclusion of these acids in the fermentation liquor increases the efficiency of production of xanthan gum to about 200% or greater.

DESCRIPTION OF SPECIFIC EMBODIMENTS

The present invention is based upon the discovery that an organic acid selected from the group consisting of pyruvic acid, alpha-keto glutaric acid, succinic acid or mixtures thereof stimulates the production of xanthan gum in the fermentation of *Xanthomonas campestris* NRRL B-1459.

The xanthan gum produced by the process of this invention comprises the native polysaccharide B-1459 which is the acetyl-ester form of a polymer comprising mannose, glucose, and glucuronic acid (as the potassium salt) in the approximate ratio of 2:1:1. The acetyl groups comprise 4.7% of the native polymer and are present as the ester of a sugar alcoholic hydroxyl group, that is, as the O-acetyl. The precipitation of the native form of the polysaccharides requires the presence of both inorganic salt and a nonsolvent, e.g. 2% potassium chloride and 56% methanol.

In accordance with this invention, a nutrient medium containing a carbon source comprising at least one sugar and a source of citric acid such as citric acid, citric acid monohydrate, a water soluble citric acid salt. The use of the citric acid source is preferred since increased production is obtained therewith. In addition, the nutrient medium contains the usual nutrient additives. To the nutrient medium is added a source of pyruvic acid, alpha-keto-glutaric acid and/or succinic acid as a stimulator for the conversion of the carbon sources to xanthan gum. Suitable sources of these stimulatory acids include the free acids, water soluble acid salts such as the sodium salt, potassium salt, and esters such as the methyl, ethyl or isopropyl esters. The preferred stimulatory organic acid is succinic acid or a source thereof, particularly in amounts of between about 0.6 and 1.0 weight/volume percent based upon the weight of the sodium salt. The nutrient medium is adjusted to a pH of between about 6.8 and about 7.2, autoclaved, cooled and then mixed with a culture of the bacterium *Xanthomonas campestris* strain NRRL B-1459. The resultant composition then is cultured at a conventional temperature such as between about 24° C. and about 26° C. with continuous agitation and aeration for about 72 to about 96 hours.

The crude xanthan gum then is isolated by first diluting the fermentation medium to less than 100 centipoises with 33 volume percent ethanol. The bacterial cells then are removed from the fermentation medium by centrifugation. Removal of the cells can be either preceded by or followed by the introduction of a water soluble alcohol such as methanol, ethanol, isopropanol or the like which is utilized subsequently to effect precipitation of the xanthan gum from the fermentation medium. Precipitation is effected by the combination of the alcohol and a salt such as potassium chloride, which is added in an amount of about 1 weight/volume percent based upon the volume of water. Subsequent to or concomitant with the introduction of the precipitating salt, the precipitating 95% ethanol is added to the fermentation medium in a concentration effective to promote precipitation of the xanthan gum. A gelatinous flocculant precipitate of low density is separated by centrifugation and is purified such as by slurrying it in 70% ethanol, redissolving it with 33% ethanol, diluting to less than 50 centipoises, followed by precipitation with the salt and the alcohol. The resultant precipitate then can be further purified as above and dried in a conventional manner and is useful for the purposes set forth above.

The following examples illustrate the present invention and are not intended to limit the same.

EXAMPLE I 50 ml of a basal nutrient medium of the following composition plus additives was sterilized for 15 minutes at 121° C. in 250 ml Erlenmeyer flasks. Glucose and the stimulatory organic acid salts were autoclaved separately and added aseptically to the rest of the medium.

| Component | Amount |
| --- | --- |
| Glucose | 20 g |
| Citric acid monohydrate | 2.19 g |
| $(NH_4)_2SO_4$ | 2.0 g |
| $KH_2PO_4$ | 5.0 g |
| $MgSO_4 \cdot 7H_2O$ | 0.2 g |
| $CaCl_3$ | 0.02 g |
| ZnO | 0.006 g |
| $FeCl_3 \cdot 6H_2O$ | 0.0024 g |
| $H_3BO_3$ | 0.006 g |
| HCL | 0.13 ml |
| Distilled Water | 1000 ml |

The preferred pH value after sterilization is 7.0 but can be between 6 and 8. After cooling, the solution was seeded with 1 ml of a washed cell suspension of X. campestris NRRL B-1459 which had been grown in the same basal medium (no additives) for 4 days. The flasks were incubated on the shaker for 4 days at 25° C. and 250 vpm. Viscosity measurements were done with a Brookfield viscometer type LVT, 30 rpm, spindle 4 at 25° C. 5 g aliquots of the whole broth were diluted with 50–150 ml 33% methanol (ethanol can also be used) and centrifuged to remove the cells. The gum suspension was precipitated with 50–150 ml 95% methanol (or ethanol). The resulting precipitates were washed with 20 ml 95% alcohol, dried and weighed. The α-keto glutaric acid and succinic acid were added in the forms and amounts set forth in Table I. The results in Table I show that sodium α-keto glutarate and sodium succinate stimulate xanthan production.

TABLE I

| Additives | Dry Cell Weight (DCW) (mg/kg broth) | Xanthan Production | | |
| --- | --- | --- | --- | --- |
| | | Viscosity (Centipoises) | Gravimetric (mg/kg broth) | Specific (mg/mg DCW) |
| None | 1,770 | 1,980 | 7,480 | 4.2 |
| 0.2% Na-α-keto-glutarate | 1,330 | 2,520 | 9,310 | 7.0 |
| 0.2% Na succinate | 1,210 | 2,540 | 8,880 | 7.3 |

EXAMPLE II

By the procedure of Example I, runs were repeated with sodium α-keto-glutarate and sodium succinate as well as with sodium pyruvate. As shown in Table II, sodium pyruvate also stimulates xanthan gum production.

TABLE II

| Additives | Dry Cell Weight (DCW) (mg/kg broth) | Xanthan Production | | |
| --- | --- | --- | --- | --- |
| | | Viscosity (Centipoises) | Gravimetric (mg/kg broth) | Specific (mg/mg DCW) |
| None | 1,460 | 1,400 | 8,900 | 6.1 |
| 0.2 Na-α-keto-glutarate | 990 | 2,070 | 10,580 | 10.7 |
| 0.2% Na succinate | 960 | 1,690 | 8,810 | 9.2 |
| 0.2% Na pyruvate | 530 | 2,340 | 11,800 | 22.3 |

EXAMPLE III

This example follows the same procedure of Example I, except that glucose was omitted from the basal medium. The data in Table III shows that the organic acids (in the absence of glucose) do not serve as a carbon source for xanthan production. They only serve as a stimulant when sugar is also present. In this example, growth is determined both by absorbance (Klett units) and by DCW.

TABLE III

| Additives | Growth (Klett Units) | Growth DCW (mg/kg broth) | Xanthan Production | |
| --- | --- | --- | --- | --- |
| | | | Viscosity (Centipoises) | Specific (Centipoises/Klett unit) |
| Na pyruvate 0.1% | 108 | — | <10 | <1 |
| Na pyruvate 0.3% | 175 | — | <10 | <1 |
| Na pyruvate 0.5% | 189 | — | <10 | <1 |
| Na pyruvate 1.0% | 252 | — | <10 | <1 |
| Na pyruvate 2.0% | 340 | — | <10 | <1 |
| Na pyruvate 3.0% | 170 | — | <10 | <1 |
| Na succinate 0.1% | 91 | — | <10 | <1 |
| Na succinate 0.2% | 93 | — | <10 | <1 |
| Na succinate 0.4% | 103 | — | <10 | <1 |
| Na succinate 0.6% | 92 | — | <10 | <1 |
| Na succinate 0.8% | 119 | — | <10 | <1 |
| Na succinate 1.0% | 135 | — | <10 | <1 |
| Na succinate 1.5% | 169 | — | <10 | <1 |
| Na succinate 2.0% | 190 | — | <10 | <1 |
| Glucose 2% + Na pyruvate 0.1% | 445 | 2440 | 3740 | 8.4 |
| Glucose 2% + Na pyruvate 0.3% | 425 | 2120 | 428 | 10.1 |
| Glucose 2% + Na pyruvate 0.5% | 405 | 1940 | 3700 | 9.1 |
| Glucose 2% + Na pyruvate 1.0% | 387 | 1480 | 2700 | 7.0 |
| Glucose 2% + Na pyruvate 2.0% | 350 | 1500 | 40 | 0.1 |
| Glucose 2% + Na pyruvate 3.0% | 86 | 175 | <10 | <0.1 |
| Glucose 2% + Na succinate 0.1% | 485 | 4240 | 3040 | 6.3 |
| Glucose 2% + Na succinate 0.2% | 452 | 3100 | 3000 | 6.6 |
| Glucose 2% + Na succinate 0.4% | 440 | 2140 | 3600 | 8.2 |
| Glucose 2% + Na succinate 0.6% | 420 | 2100 | 3700 | 8.8 |
| Glucose 2% + Na succinate 0.8% | 400 | 1800 | 3520 | 8.8 |
| Glucose 2% + Na succinate 1.0% | 395 | 1750 | 3400 | 8.6 |

TABLE III-continued

| Additives | Growth (Klett Units) | Growth DCW (mg/kg broth) | Xanthan Production Viscosity (Centipoises) | Specific (Centipoises/Klett unit) |
|---|---|---|---|---|
| Glucose 2% + Na succinate 2.0% | 395 | 1750 | 2400 | 6.1 |
| Glucose 2% + Na succinate 3.0% | 380 | 1600 | 1120 | 3.0 |

— = not done

EXAMPLE IV

This example follows the same procedure of Example III, i.e. glucose, was omitted from the basal medium. Table IV shows again that the organic acids are only stimulatory in the presence of sugar.

TABLE IV

| Additive | Growth (Klett Units) | Xanthan Production Viscosity (Centipoises) | Specific (Centipoises/Klett Unit) |
|---|---|---|---|
| None | 68 | <10 | <1 |
| Na α-keto-glutarate 0.1% | 120 | <10 | <1 |
| Na α-keto-glutarate 0.2% | 140 | <10 | <1 |
| Na α-keto-glutarate 0.4% | 152 | <10 | <1 |
| Na α-keto-glutarate 0.6% | 204 | <10 | <1 |
| Na α-keto-glutarate 0.8% | 202 | <10 | <1 |
| Na α-keto-glutarate 1.0% | 234 | <10 | <1 |
| Na α-keto-glutarate 2.0% | 224 | <10 | <1 |
| Na α-keto-glutarate 3.0% | 160 | <10 | <1 |
| Glucose 2% + Na α-keto-glutarate 0.1% | 715 | 3600 | 5.0 |
| Glucose 2% + Na α-keto-glutarate 0.2% | 750 | 3520 | 4.7 |
| Glucose 2% + Na α-keto-glutarate 0.4% | 620 | 4040 | 6.5 |
| Glucose 2% + Na α-keto-glutarate 0.6% | 630 | 3700 | 5.9 |
| Glucose 2% + Na α-keto-glutarate 0.8% | 665 | 3880 | 5.8 |
| Glucose 2% + Na α-keto-glutarate 1.0% | 707 | 3660 | 5.2 |
| Glucose 2% + Na α-keto-glutarate 2.0% | 750 | 2360 | 3.1 |
| Glucose 2% + Na α-keto-glutarate 3.0% | 400 | 20 | 0.05 |

EXAMPLE V

This example follows the same procedure as Example I except that 4% sucrose was used instead of 2% glucose. Table V shows that the organic acids are also stimulatory when sucrose is the major carbon source.

TABLE V

| Additive | Growth (Klett Units) | Xanthan Production Viscosity (Centipoises) | Specific Centipoises/Klett Units |
|---|---|---|---|
| None | 720 | 4700 | 6.5 |
| Na pyruvate 0.1% | 628 | 5120 | 8.4 |
| Na pyruvate 0.3% | 654 | 8460 | 12.9 |
| Na pyruvate 0.5% | 670 | 11180 | 16.6 |
| Na pyruvate 1.0% | 490 | 10020 | 20.4 |
| Na pyruvate 1.5% | 430 | 2440 | 5.6 |
| Na pyruvate 2.0% | 430 | 830 | 1.9 |
| Na pyruvate 3.0% | 400 | 40 | 0.1 |
| Na α-keto-glutarate 0.1% | 650 | 6690 | 10.3 |
| Na α-keto-glutarate 0.2% | 610 | 8140 | 13.3 |
| Na α-keto-glutarate 0.4% | 525 | 10700 | 20.4 |
| Na α-keto-glutarate 0.6% | 613 | 11200 | 18.2 |
| Na α-keto-glutarate 0.8% | 605 | 9800 | 16.1 |
| Na α-keto-glutarate 1.0% | 670 | 8540 | 12.7 |
| Na α-keto-glutarate 1.5% | 575 | 4000 | 6.8 |
| Na α-keto-glutarate 2.0% | 575 | 1420 | 2.4 |
| Na α-keto-glutarate 3.0% | 500 | 50 | 0.1 |
| Na succinate 0.1% | 605 | 5060 | 8.3 |
| Na succinate 0.2% | 565 | 6380 | 11.3 |
| Na succinate 0.4% | 590 | 8500 | 14.4 |
| Na succinate 0.6% | 535 | 12280 | 22.9 |
| Na succinate 0.8% | 570 | 12400 | 21.7 |
| Na succinate 1.0% | 595 | 14340 | 24.1 |
| Na succinate 1.5% | 576 | 10300 | 17.8 |
| Na succinate 2.0% | 525 | 3940 | 7.5 |
| Na succinate 3.0% | 460 | 1420 | 3.1 |

EXAMPLE VI

This example follows the procedure of Example I except that 4% sucrose was used instead of 2% glucose. The results are shown in Table VI.

TABLE VI

| Additive | Growth (Klett Units) | Xanthan Production Viscosity (Centipoises) | Gravimetric (mg/kg broth) | Specific (Centipoises/Klett Unit) |
|---|---|---|---|---|
| None | 960 | 7120 | 24000 | 7.4 |
| Na pyruvate, 0.5% | 740 | 16200 | 32040 | 21.9 |
| Na α-keto-glutarate, 0.6% | 850 | 11540 | 27400 | 13.6 |
| Na succinate, 1% | 770 | 14820 | 30400 | 19.2 |

EXAMPLE VII

This example follows the procedure of Example I except that 2% sucrose was used instead of 2% glucose. The duration of the experiment was 48 hours. The results are shown in Table VII.

TABLE VII

| Additive | Growth (Klett Units) | Growth DCW (mg/kg broth) | Xanthan Production Viscosity (Centipoises) | Xanthan Production Specific (Centipoises/Klett Unit) |
| --- | --- | --- | --- | --- |
| None | 660 | 1900 | 4300 | 6.5 |
| Na pyruvate 0.1% | 710 | 2300 | 4660 | 6.6 |
| Na pyruvate 0.3% | 670 | 1900 | 5600 | 8.4 |
| Na pyruvate 0.5% | 730 | 2500 | 6320 | 8.7 |
| Na pyruvate 0.75% | 750 | 2500 | 6040 | 8.1 |
| Na pyruvate 1.5% | 710 | 2500 | 2500 | 3.2 |
| Na αketo-glutarate 0.12% | 660 | 2200 | 4660 | 7.1 |
| Na αketo-glutarate 0.36% | 660 | 2100 | 5700 | 8.7 |
| Na αketo-glutarate 0.6% | 720 | 2300 | 5900 | 8.2 |
| Na αketo-glutarate 0.75% | 700 | 2100 | 5600 | 8.0 |
| Na αketo-glutarate 1.5% | 780 | 2500 | 3540 | 4.5 |
| Na succinate 0.1% | 520 | 2000 | 4540 | 8.7 |
| Na succinate 0.3% | 620 | 2500 | 4640 | 7.5 |
| Na succinate 0.6% | 670 | 2300 | 5400 | 8.1 |
| Na succinate 1.0% | 660 | 2000 | 5400 | 8.2 |
| Na succinate 2.0 | 780 | 2500 | 4920 | 6.3 |

We claim:

1. In the process for the production of xanthan gum by the fermentative conversion of a nutrient composition containing a sugar carbon source with the bacterium *Xanthomonas campestris* NRRL B-1459, the improvement which comprises adding to said nutrient medium an organic acid that stimulates the conversion to xanthan gum, said organic acid selected from the group consisting of α-keto glutaric acid, pyruvic acid, salts thereof, esters thereof and mixtures thereof.

2. The process of claim 1 wherein the organic acid is α-keto glutaric acid.

3. The process of claim 2 wherein the nutrient composition contains a source of citric acid.

4. The process of claim 1 wherein the organic acid is pyruvic acid.

5. The process of claim 4 wherein the nutrient composition contains a source of citric acid.

6. The process of claim 1 wherein the nutrient composition contains a source of citric acid.

* * * * *